United States Patent
Van Osten, III (10) Patent No.: US 9,138,278 B2
(45) Date of Patent: Sep. 22, 2015

(54) SUPRAPATELLAR SYSTEM AND METHOD

(71) Applicant: Zimmer, Inc., Warsaw, IN (US)

(72) Inventor: G. Karl Van Osten, III, Tupelo, MS (US)

(73) Assignee: Zimmer, Inc., Warsaw, IN (US)

( * ) Notice: Subject to any disclaimer, the term of this patent is extended or adjusted under 35 U.S.C. 154(b) by 179 days.

(21) Appl. No.: 13/886,379

(22) Filed: May 3, 2013

(65) Prior Publication Data

US 2013/0310886 A1 Nov. 21, 2013

Related U.S. Application Data (60) Provisional application No. 61/642,808, filed on May 4, 2012.

(51) Int. Cl.
*A61B 17/88* (2006.01)
*A61B 17/17* (2006.01)

(52) U.S. Cl.
CPC ............. *A61B 17/88* (2013.01); *A61B 17/1717* (2013.01)

(58) Field of Classification Search
CPC ............................. A61B 17/88; A61B 17/1717
USPC ............. 606/80, 86 R, 87–89, 90, 95, 96–99, 606/329; 600/201–246
See application file for complete search history.

(56) References Cited

U.S. PATENT DOCUMENTS

| | | | | |
|---|---|---|---|---|
| 5,197,971 | A * | 3/1993 | Bonutti ........................ | 606/192 |
| 7,476,225 | B2 | 1/2009 | Cole | |
| 8,257,361 | B2 | 9/2012 | Ritchey et al. | |
| 8,328,805 | B2 | 12/2012 | Cole | |
| 2012/0143010 | A1* | 6/2012 | Deasey et al. ................. | 600/207 |
| 2013/0006258 | A1* | 1/2013 | Ritchey et al. ................. | 606/96 |
| 2013/0172890 | A1* | 7/2013 | Limouze et al. ................ | 606/62 |

FOREIGN PATENT DOCUMENTS

DE  EP2617370  * 7/2013

OTHER PUBLICATIONS

Eastman, J. G, et al., "Retropatellar Technique for Intramedullary Nailing of Proximal Tibia Fractures: A Cadaveric Assessment", J Orthop Trauma., 24(11), (Nov. 2010), 672-676.
Eastman, J. G, et al., "The retropatellar portal as an alternative site for tibial nail insertion: a cadaveric study", J Orthop Trauma., 24(11), (Nov. 2010), 659-64.
Gelbke, M. K, et al., "Suprapatellar versus infra-patellar intramedullary nail insertion of the tibia: a cadaveric model for comparison of patellofemoral contact pressures and forces", J Orthop Trauma., 24(11), (Nov. 2010), 665-71.
Morandi, Max, et al., "Intramedullary Nailing of Tibial Fractures: Review of Surgical Techniques and Description of a Percutaneous Lateral Suprapatellar Approach", Orthopedics, 33(3), [Online]. Retrieved from the Internet: <URL: http://www.healio.com/orthopedics/knee/journals/ortho/%7B044d928d-d948-434f-a658-36cc26bcb2c1%7D/intramedullary-nailing-of-tibial-fractures-review-of-surgical-techniques-and-description-of-a-percutaneous-latera>, (Mar. 2010), 11 pgs.

* cited by examiner

*Primary Examiner* — Christopher Beccia
(74) *Attorney, Agent, or Firm* — Schwegman Lundberg & Woessner, P.A.

(57) ABSTRACT

Suprapatellar systems, system components, and methods of operating on a tibial fracture of a patient are disclosed. A method can include making an incision proximal to a patella of a knee joint, forming an operation space, and inserting a portion of a retractor in the operation space to define an entry canal. The retractor can be inserted in a low profile configuration and, once positioned as desired by a surgeon, expanded to a high profile configuration. Expansion of the retractor can expand the operation space in at least one of an anterior-posterior direction or a medial-lateral direction and can increase a diameter of the entry canal. The method can further include inserting a trocar, having at least one guide hole, in the entry canal and guiding a guide pin through the at least one guide hole and into a tibia.

20 Claims, 10 Drawing Sheets

SUPRAPATELLAR SYSTEM AND METHOD

CLAIM OF PRIORITY

This patent document claims the benefit of priority under 35 U.S.C. §119(e) of VanOsten, U.S. Provisional Patent Application Ser. No. 61/642,808, entitled "SUPRAPATELLAR SYSTEM AND METHOD," filed on May 4, 2012, which is herein incorporated by reference in its entirety.

TECHNICAL FIELD

This patent document pertains generally to a method for insertion of a tibial nail, and more specifically, to a suprapatellar method for insertion of a tibial nail.

BACKGROUND

Tibial fractures, such as a tibial shaft fracture, can occur between an ankle and a knee joint of a patient. Fractures of the tibia can be serious due to their potential for nonunion, malunion, or long-term dysfunction, as well as their propensity for open injury. Although some tibial fractures can be repaired by a long leg cast, other tibial fractures, such as fractures that have displaced or altered an angulation of the tibia, can require surgery to secure one or more bone portions.

Existing surgical methods to repair a tibial fracture are invasive. Methods for repairing an anterior tibial shaft fracture can include, for example, inserting an intramedullary rod, such as a tibial rod or a tibial nail, through a tibial plateau and into an intramedullary canal of a tibia. These anterior methods include placing a leg in flexion, such that a knee joint is bent at an angle less than about 150° and greater than about 30° of flexion. The flexion state of the knee joint presents a surgeon with a large number of muscles around the surgical site, which increases the invasiveness of the method and the post-operation pain or recovery time. For example, the anterior tibial shaft fracture repair method can include splitting a patellar tendon to access the tibial plateau or cutting through a fat pad of the knee joint.

SUMMARY

The present inventor recognizes that a patient may experience increased pain in or around a knee joint when a patellar tendon or fat pad is severed to gain access to a tibial plateau and an intramedullary canal of a tibia.

Suprapatellar systems, system components, and methods of operating on a tibial fracture of a patient are disclosed and provide the advantage of avoiding nerves associated with the fat pad and minimize irritation of cartilage and tendons in the knee joint. A method can include making an incision proximal to a patella of a knee joint, forming an operation space, and inserting a portion of a retractor in the operation space to define an entry canal. The retractor can be inserted in a low profile configuration and, once positioned as desired by a surgeon, expanded to a high profile configuration. Expansion of the retractor can expand the operation space in at least one of an anterior-posterior direction or a medial-lateral direction and increase a diameter of the entry canal. The method can further include inserting a trocar, having at least one guide hole, in the entry canal and guiding a guide pin through the at least one guide hole and into a tibia. Prior to removal, the retractor can be adjusted from the high profile configuration back to the low profile configuration.

To better illustrate the suprapatellar methods disclosed herein, a non-limiting list of examples is provided here:

In Example 1, a method can comprise making an incision proximal to a patella of a knee joint, forming an operation space between the patella and the knee joint, inserting a portion of a retractor, in a low profile configuration, in the operation space, including partially defining an entry canal through the operation space, adjusting at least the portion of the retractor in the operation space from the low profile configuration to a high profile configuration, inserting a trocar having at least one guide hole in the entry canal, and guiding a guide pin through the at least one guide hole and into a tibia.

In Example 2, the method of Example 1 is optionally configured such that adjusting the retractor from the low profile configuration to the high profile configuration includes expanding the operation space in at least one of an anterior-posterior direction or a medial-lateral direction.

In Example 3, the method of any one or any combination of Examples 1-2 is optionally configured such that adjusting the retractor from the low profile configuration to the high profile configuration includes increasing a diameter of the entry canal.

In Example 4, the method of any one or any combination of Examples 1-3 is optionally configured such that adjusting the retractor from the low profile configuration to the high profile configuration includes increasing a spacing been a posterior side of the patella and an adjacent surface of the tibia or a femur.

In Example 5, the method of any one or any combination of Examples 1-4 is optionally configured adjusting the retractor from the low profile configuration to the high profile configuration includes stretching one or more viscoelastic tissues associated with the patella.

In Example 6, the method of any one or any combination of Examples 1-5 is optionally configured to further comprise adjusting the retractor from the high profile configuration to the low profile configuration and removing the retractor from the operating space.

In Example 7, the method of any one or any combination of Examples 1-6 is optionally configured such that inserting the portion of the retractor in the operation space includes engaging a concave outer surface of the retractor with a posterior side of the patella.

In Example 8, the method of any one or any combination of Examples 1-7 is optionally configured to further comprise placing the knee joint in an extension position prior to making the incision, including forming an angle of about 150 degrees or more between a femur and the tibia.

In Example 9, the method of any one or any combination of Examples 1-8 is optionally configured such that making the incision proximal to the patella includes making an incision at least 1.5 centimeters proximal to the patella.

In Example 10, the method of any one or any combination of Examples 1-9 is optionally configured such that making the incision proximal to the patella includes making an incision in a quadriceps tendon.

In Example 11, the method of any one or any combination of Examples 1-10 is optionally configured to further comprise inserting a tube in the entry canal prior to inserting the trocar, and wherein inserting the trocar includes inserting the trocar in the tube.

In Example 12, the method of any one or any combination of Examples 1-11 is optionally configured to further comprise adjusting a position of the guide pin, including moving the guide pin at least about 2 millimeters in at least one of a medial-lateral direction or an anterior-posterior direction.

In Example 13, the method of any one or any combination of Examples 1-12 is optionally configured such that forming the operation space includes loosening at least a portion of one or more viscoelastic tissues connected to the patella.

In Example 14, a method can comprise positioning a knee joint in an extension orientation, forming an operation space between a patella and the knee joint from a suprapatellar direction with a retractor defining an entry canal, expanding a portion of the retractor from a low profile configuration, in which the entry canal has a first diameter, to a high profile configuration, in which the entry canal has a larger second diameter, inserting a guide pin through the entry canal and into at least a portion of a tibia through at least a portion of the operation space from the suprapatellar direction, opening a proximal canal of the tibia, inserting a guide rod in at least a portion of the proximal canal, and inserting a tibial nail in the portion of the proximal canal.

In Example 15, the method of Example 14 is optionally configured such that opening the proximal canal includes using at least one of an entry reamer or an entry awl inserted in a portion of the tibia from the suprapatellar direction.

In Example 16, the method of any one or any combination of Examples 14-15 is optionally configured to further comprise measuring a tibial nail length with a nail length gauge.

In Example 17, the method of any one or any combination of Examples 14-16 is optionally configured to further comprise reducing a fracture of the tibia.

In Example 18, the method of any one or any combination of Examples 14-17 is optionally configured to further comprise reaming the opened proximal canal with a reamer guided over the guide rod.

In Example 19, a method can comprise positioning a knee joint in an extension orientation, making an incision proximal to a patella of the knee joint, forming an operation space, using the incision, between a portion of the patella and a compartment of the knee joint, inserting, from a suprapatellar direction, a portion of a retractor in a low profile configuration into the operation space, expanding the operation space and defining an entry canal, including at least partially anteriorly disposing the patella from the compartment of the knee joint by adjusting the portion of the retractor from the low profile configuration to a high profile configuration, inserting a reamer through the entry canal to open a proximal canal of the tibia, and inserting a reduction rod in at least a portion of the proximal canal.

In Example 20, the method of Example 19 is optionally configured such expanding the operation space includes resting a portion the retractor on a femur and anteriorly adjusting an opposing portion of the retractor.

In Example 21, the method of anyone one or any combination of Examples 1-20 is optionally configured such that all elements or options recited are available to use of select from.

This Summary is intended to provide non-limiting examples of the present subject matter—it is not intended to provide an exclusive or exhaustive explanation. The Detailed Description below is included to provide further information about the present suprapatellar methods and related systems and system components.

BRIEF DESCRIPTION OF THE DRAWINGS

In the drawings, which are not necessarily drawn to scale, like numerals can be used to describe similar elements throughout the several views. The drawings illustrate generally, by way of example, but not by way of limitation, various embodiments discussed in the present document.

DETAILED DESCRIPTION

The present disclosure describes suprapatellar systems, system components, and methods of operating on a tibial fracture of a patient. The suprapatellar systems, system components, and methods can be performed while a patient's knee joint is in an extension orientation, such as an orientation defined by an angle greater than about 150 degrees between a femur and a tibia. While the knee joint is in extension, leg muscles (e.g., those muscles surrounding or associated with the knee joint) are typically more relaxed than when the knee joint is in a flexion orientation. It has been found that relaxed muscles can aid in reducing the tibial fracture, as compared to when muscles are engaged or in tension resulting from the flexion orientation. Further, positioning the knee joint in flexion requires a surgeon to go through an anterior side of the knee joint, such as through the fat pad, to access a tibial plateau. It is believed that half of tibial fracture patients that undergo a tibial nail insertion complain of post-operation pain in an anterior or fat pad region of the knee joint. Positioning the knee joint in extension allows the surgeon to access the tibial plateau from a suprapatellar direction, such as underneath a patella or a posterior side of the patella, thereby avoiding nerves associated with the fat pad of the knee joint. Further, suprapatellar methods provide the benefit of minimizing irritation of cartilage in the knee joint during operation. For example, the suprapatellar methods discussed herein can include system generally sized and shaped with smaller diameter and cross-sections than system components associated with the anterior method.

Figure 1:
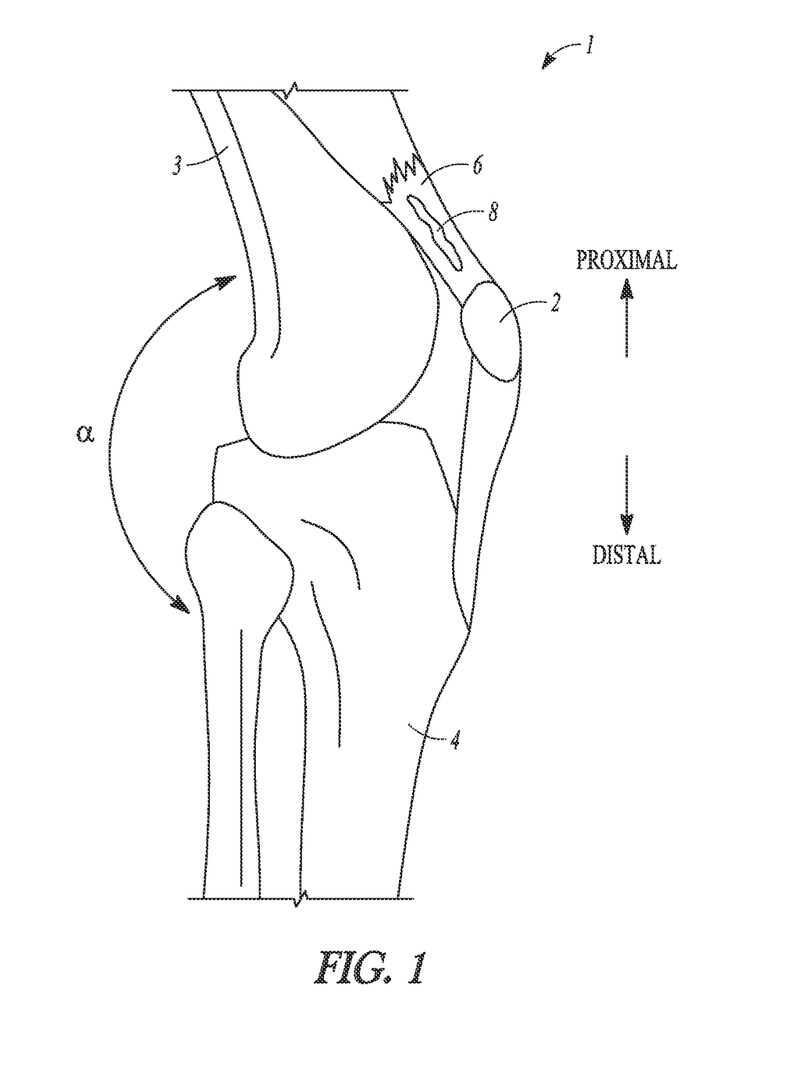
FIG. 1 is a perspective view of a knee joint in an extension orientation, in accordance with at least one example of the present invention.

FIG. 1 is a perspective view of a knee joint 1 in an extension orientation, such as when a leg is relatively straight. The extension orientation can include an angle α between a femur 3 and a tibia 4 of greater than about 150 degrees or about 30 degrees of flexion. In an example, the knee joint can be positioned at the angle α between about 165 and about 170 degrees, inclusive, or about 15 to 10 degrees of flexion for an operation on a tibial fracture. Positioning the knee joint 1 in extension can relax viscoelastic tissues 6 associated with the knee joint 1, such that muscles or tendons associated with or surrounding the knee joint can be readily moved by the surgeon. These muscles or tendons can include, for example, a quadriceps muscle, a quadriceps tendon, a lateral patellar retinaculum, or a patellar tendon.

An incision 8 can be made proximal to a patella 2. The incision 8 can extend in a proximal-distal direction or a medial-lateral direction. In an example, the incision 8 can be at least about 1.5 centimeters proximal to the patella. The incision 8 can be at least about 3 millimeters in length. In an example, the incision 8 can be disposed laterally of the knee 1 to permit reaming in a distal direction, slightly angled laterally to medially. In an example, the incision 8 can be made about 2 finger widths above a superolateral corner of the patella 2.

Figure 2A:
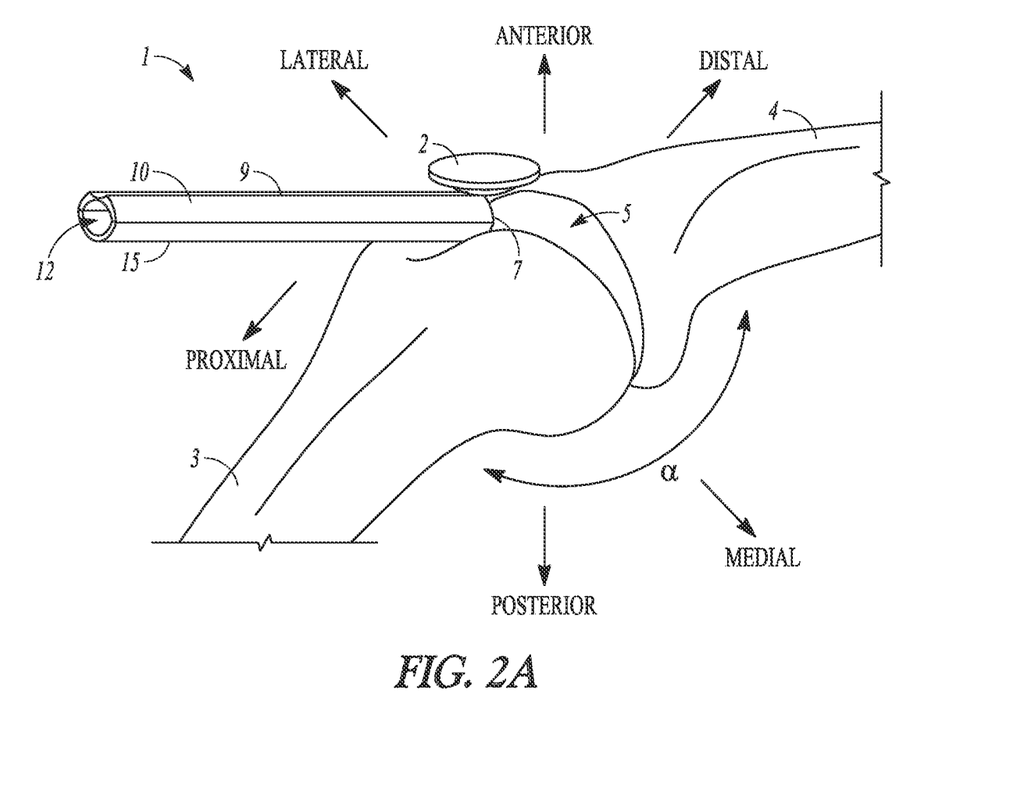
FIG. 2A is a perspective view of a suprapatellar system, including a retractor in a low profile configuration, in accordance with at least on example of the present invention.

FIG. 2A is a perspective view of a suprapatellar system including a retractor 10. As illustrated, the refractor 10 can assume a low profile configuration and a distal end 7 can be configured to engage an operation space 5, such as underneath the patella 2 through an incision (8, FIG. 1). The operation space 5 can be initially formed by an surgeon loosening the muscles or tendons holding the patella 2 in place, such as by inserting his/her fingers or other device in the knee joint 1 and pushing or pulling anteriorly on the patella 2. The retractor 10 can define an entry canal 12 configured to receive various suprapatellar system components. In an example, the retractor 10 can include an outer surface configured to facilitate retention within the operation space 5, such as at least one of a textured surface or a matte finish. At least a portion of the outer surface of the refractor can include a material to help distribute loads on at least one of the patella or the femur, such as memory foam, to potentially reduce pressure in a region of the patella-femoral joint.

Figure 2B:
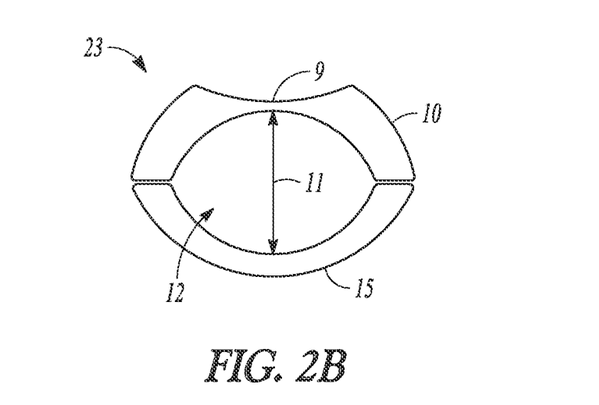
FIG. 2B is a cross-sectional view of a proximal portion of the retractor of FIG. 2A, in accordance with at least one example of the present invention.

FIG. 2B is a cross-sectional view of a proximal portion of the retractor 10 in a low profile configuration 23. The low profile configuration 23 can include a diameter 11 permitting insertion of the retractor 10 in the operation space (5, FIG. 2A). That is, the diameter 11 can be sized to fit in a manually formed operation space. Further, the diameter 11 can define an upper or lower boundary of the entry canal 12. The refractor 10 can be sized or shaped to be inserted in the operation space with minimal resistance from components of the knee joint 1. In an example, the retractor 10 can include a tapered distal end (7, FIG. 2A) configured to facilitate insertion in the operation space. Further, the retractor 10 can be configured to conform to the natural anatomy of the knee joint 1, such as a posterior side of the patella 2. An outside concave surface 9 of the retractor 10 can be configured to receive the posterior side of the patella 2. An opposing outside convex surface 15 of the retractor can be configured to readily slide along the femur or muscle or tendon of the knee joint 1.

Figure 3A:
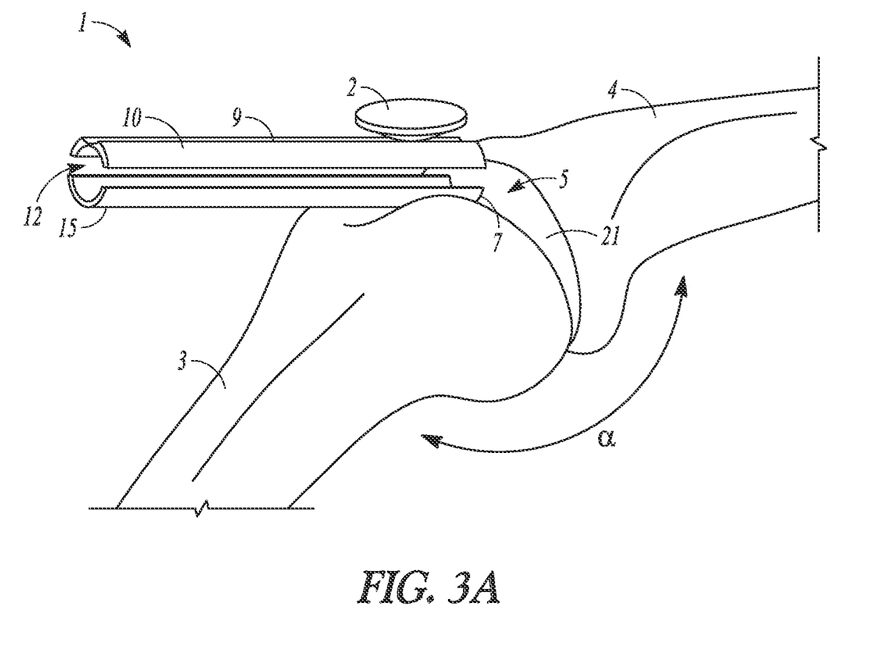
FIG. 3A is a perspective view of a suprapatellar system, including a retractor in a high profile configuration, in accordance with at least on example of the present invention.
Figure 3B:
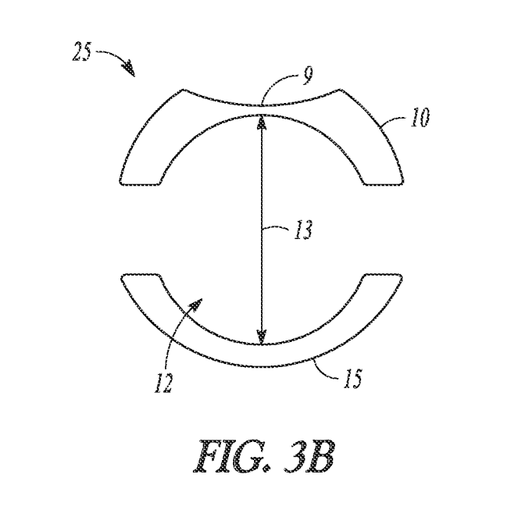
FIG. 3B is a cross-sectional view of a proximal portion of the retractor of FIG. 3A, in accordance with at least one example of the present invention.

FIG. 3A is a perspective view of the suprapatellar system including the refractor 10 in an expanded or high profile configuration 25. As shown, the retractor 10 can be further inserted in the operation space 5 so that its distal end 7 is proximate or engaging a tibial plateau 21. As shown in FIG. 3B, the high profile configuration 25 of the retractor 10 can include a diameter 13, which is larger than the diameter (11, FIG. 2B) of the low profile configuration (23, FIG. 2B), to increase a cross-sectional area of the entry canal 12. The retractor 10 can be configured to expand the operation space 5 in at least one of an anterior-posterior or medial-lateral direction to increase a distance of the patella 2 from a surface of the tibia 4 or femur 3. Increasing the size of the operation space 5 can permit larger suprapatellar system equipment to engage the tibial plateau 21 through the entry canal 12. The high profile configuration 25 can be configured to stretch viscoelastic tissues associated with the patella 2 without tearing or snapping them. In an example, the diameter 13 of the high profile configuration can return to the low profile configuration (23, FIG. 2B) to reduce the size of the operation space 5 or reduce potential irritation to the knee joint 1, including tissues and cartilage.

The retractor 10 can include a mechanism configured to expand the entry canal 12 or adjust the retractor 10 from the low profile configuration (23, FIG. 2B) to the high profile configuration 25. For example, the mechanism can be configured to move at least one of an upper jaw or a lower jaw away from the opposing jaw. In an example, the retractor 10 can include a tension gauge configured to indicate to the surgeon a compression force exerted on the retractor 10.

Figure 4:
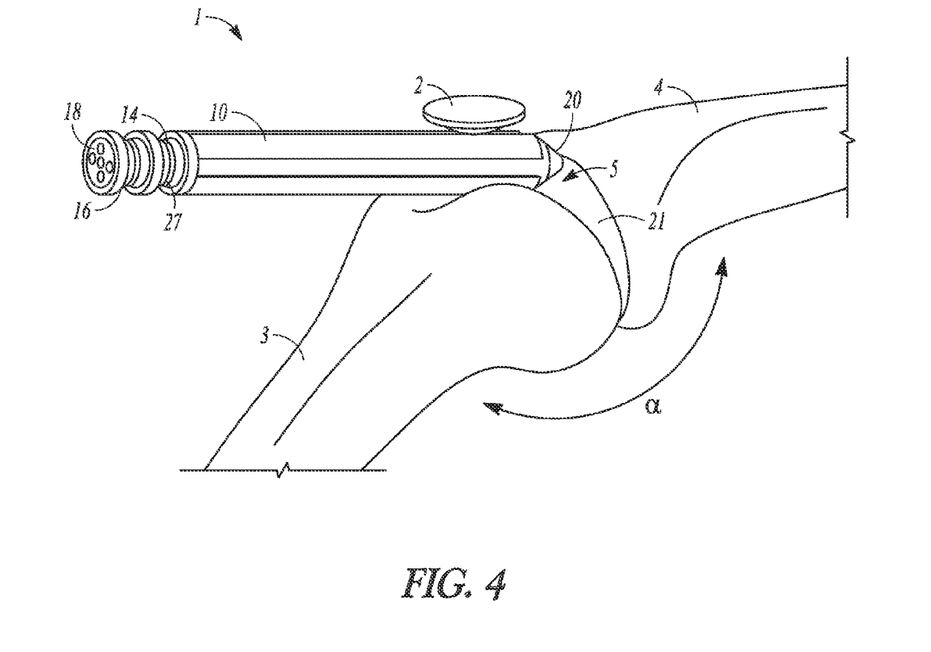
FIG. 4 is a perspective view of a suprapatellar system, including a trocar, in accordance with at least one example of the present invention.

FIG. 4 is a perspective view of the suprapatellar system including a trocar 16 and a tube 14. The tube 14 can include an outside diameter corresponding to the diameter (13, FIG. 3B) of the high profile configuration (25, FIG. 3B) of the retractor 10. In an example, the tube 14 can include a series of grooves 27 configured to aid grip during insertion of the tube 14 in at least a portion of the entry canal (12, FIG. 2A) defined by the retractor 10. In an example, the tube 14 can be made of a resorbable material, such as poly-L-lactides, poly-D-lactides, poly-DL-lactides, polyglycolides, polycaprolactones, or combinations thereof.

Figure 5A:
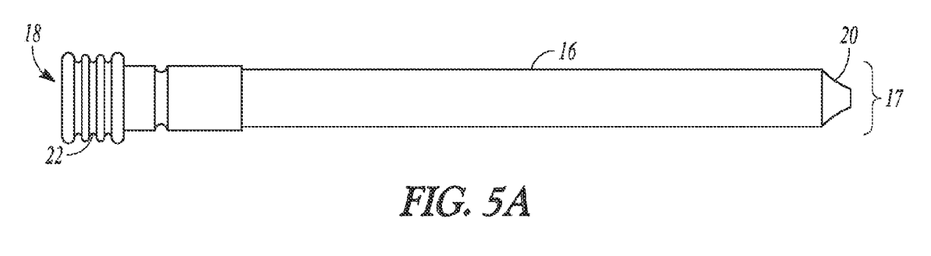
FIG. 5A is a side view of the trocar of FIG. 4, in accordance with at least one example of the present invention.

FIG. 5A is a side view of the trocar 16, which includes a trocar diameter 17. The trocar diameter 17 can correspond to an inside diameter of the tube 14, such that the trocar 16 can be received by the tube 14. The tube 14, in turn, can be received by the retractor 10 to click or lock into a desired position. The tube 14 can be configured to receive further suprapatellar system equipment, such as a reamer. The outside diameter of the tube 14 can be minimized, such that the retractor 10 high profile configuration can be minimized to reduce potential irritation to cartilage, muscle, the knee compartment, or the patella. The trocar 16 can be made of a radiolucent material, such as radiolucent carbon fibers, to permit passage of x-rays or other radiation. Further, the trocar 16 can include a series of grooves 22 configured to aid in grip during insertion of the trocar 16 into at least a portion of the tube 14.

Figure 5B:
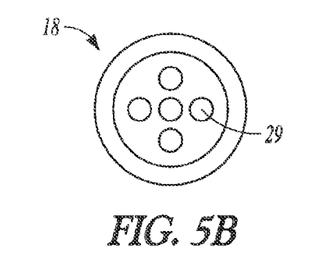
FIG. 5B is a proximal end view of the trocar of FIG. 4, in accordance with at least one example of the present invention.

The trocar 16 can include a proximal guide end 18 configured to receive at least one guide pin, as discussed herein. As shown in FIG. 5B the proximal guide end 18 can include one or more guide pin orifices 29, with each orifice configured to receive a guide pin. Although five guide pin orifices 29 are illustrated, the present trocar 16 is not limited thereto. In an example, the proximal guide end 18 includes two guide pin orifices 29. Further, the trocar 16 can include a cone distal end 20 configured to direct an orientation of the at least one guide pin inserted in the guide pin orifice 29. The distal cone end 20 can be configured to pass at least partially through the operation space 5 to at least be proximate or contact the tibial plateau 21. The trocar 16 can be configured to be received by the tube 14 to click or lock into a desired position.

Figure 6:
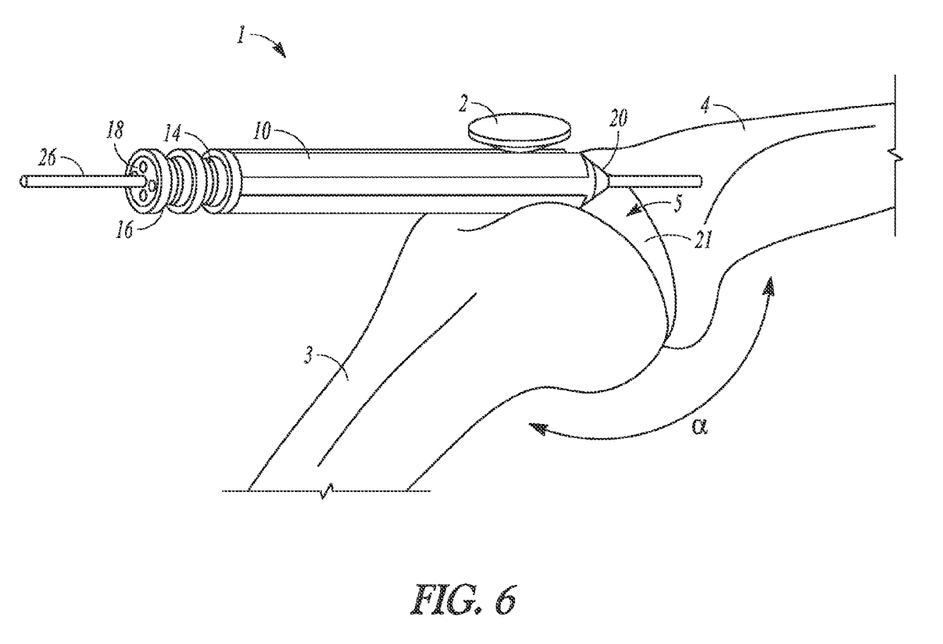
FIG. 6 is a perspective view of a suprapatellar system, including a guide pin, in accordance with at least one example of the present invention.

FIG. 6 is a perspective view of the suprapatellar system including a guide pin 26, such as received by the trocar 16. In an example, the guide pin 26 can include a disposable guide pin, such as a 3.0 millimeter diameter guide pin. The guide pin 26 can engage the tibia 4 by way of the operation space 5 and the tibial plateau 21, such as by shooting the guide pin 26 with a "Gatling gun" aimer. In an example, the trocar 16 can be removed after the guide pin 26 is engaged with the tibia 4, such the tube 14 remains in the entry canal 12 of the refractor 10.

Figure 7:
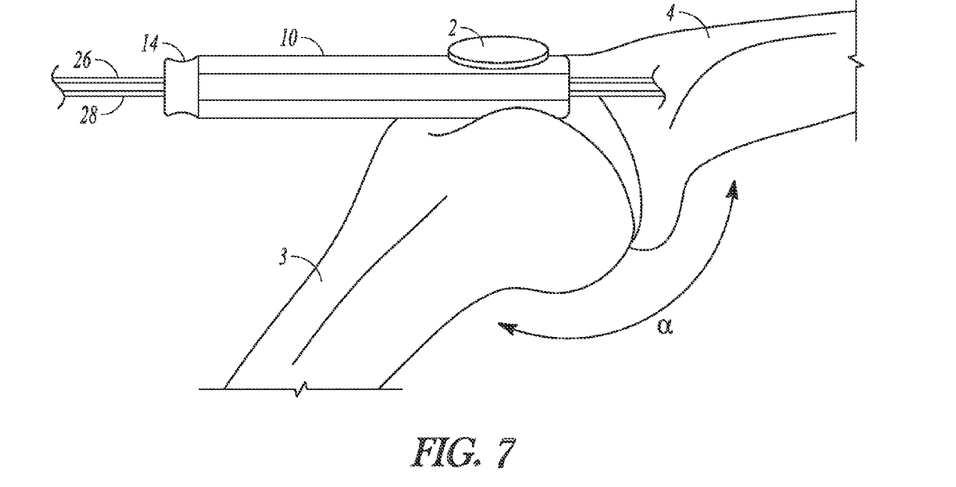
FIG. 7 is a perspective view of a suprapatellar system, including a guide pin adjuster, in accordance with at least one example of the present invention.

FIG. 7 is a perspective view of the suprapatellar system including an adjusted guide pin 28. The adjusted guide pin 28 can be adjusted by a guide pin adjuster to move the guide pin 26 in at least one of the medial-lateral direction and anterior-posterior direction, such as at least about 2 millimeters. In an example, a position of the guide pin 26 is relocated to a position of the adjusted guide pin 28 to more accurately locate a tibial tunnel or intramedullary canal of the tibia 4. In an example, an x-ray or fluorescence image guided technique can be used.

Figure 8:
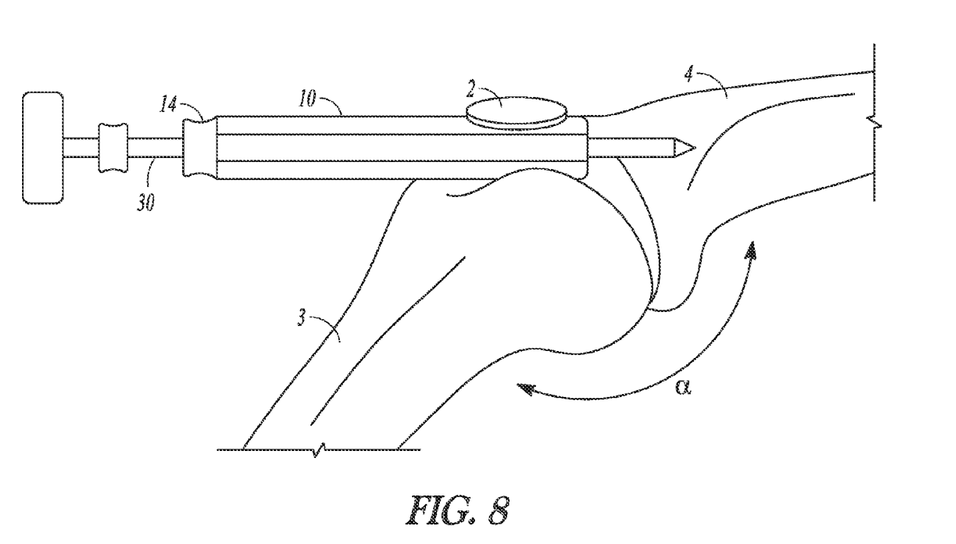
FIG. 8 is a perspective view of a suprapatellar system, including an entry awl, in accordance with at least one example of the present invention.

FIG. 8 is a perspective view of the suprapatellar system including an entry awl 30 configured to open a proximal canal of the tibia, to gain access to the intramedullary canal of the tibia 4. In an example, the entry awl 30 can be an entry reamer. To aid in opening the proximal canal, the entry awl 30 can include a sharpened awl distal end 32. The entry awl 30 can be used to open the proximal canal after at least one of the guide pin 26 or the adjusted guide pin 28 is removed from the tibia 4. In an example, the entry awl 30 can be placed over the guide pin 26 or the adjusted guide pin 28, such that the entry awl 30 is guided through the tube 14 to engage the tibial plateau 21 to provide the opening of about 3 millimeters to about 7 millimeters depth within the tibia 4. The entry awl 30 can be in the range of about 6 millimeters to about 15 millimeters in diameter and create a corresponding sized opening to the proximal canal.

Figure 9:
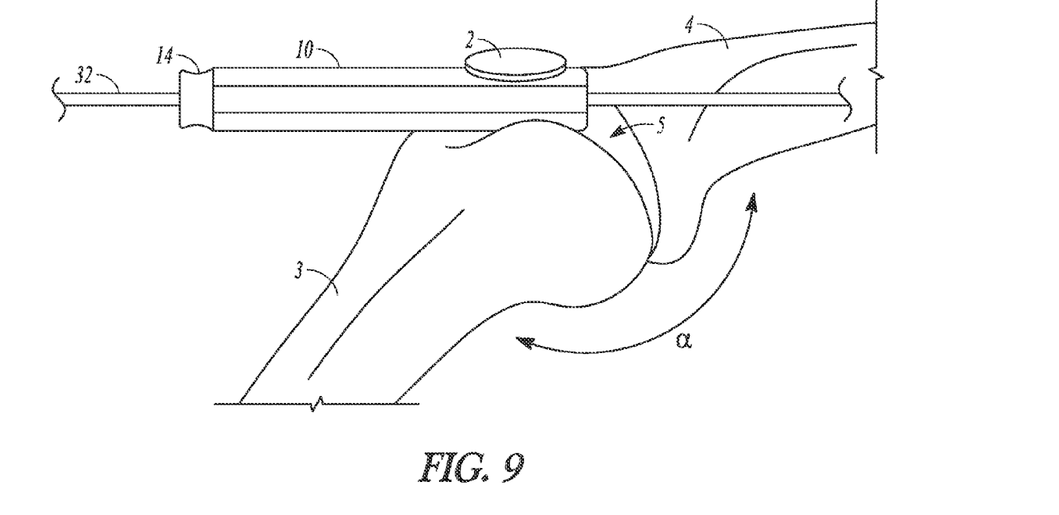
FIG. 9 is a perspective view of a suprapatellar system, including a guide rod, in accordance with at least one example of the present invention.

FIG. 9 is a perspective view of the suprapatellar system including a guide rod 32 inserted in the tibia 4, such as through the opening formed by the entry awl (30, FIG. 8). In an example, the guide rod 32 can include a length sufficient to guide a reamer, such at least about 80 centimeters in length.

Figure 10:
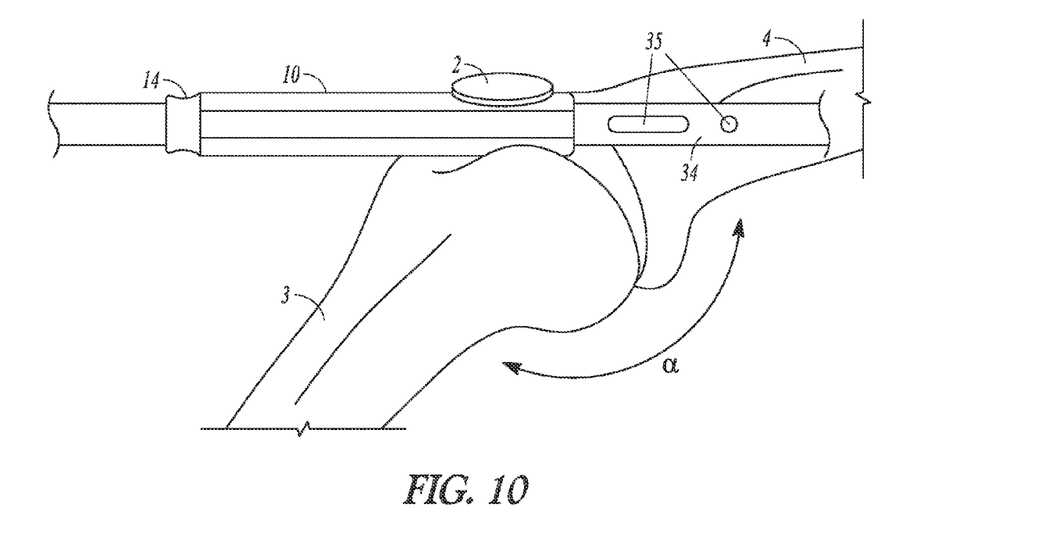
FIG. 10 is a perspective view of a suprapatellar system and a tibial nail, in accordance with at least one example of the present invention.

FIG. 10 is a perspective view of the suprapatellar system and a tibial nail 34. The tibial nail 34 can be inserted in the tibia 4. Further, the tibial nail 34 can include one or more proximal lock voids 35 configured to receive retention nails to hold the tibial nail 34 in a desired location.

Figure 11:
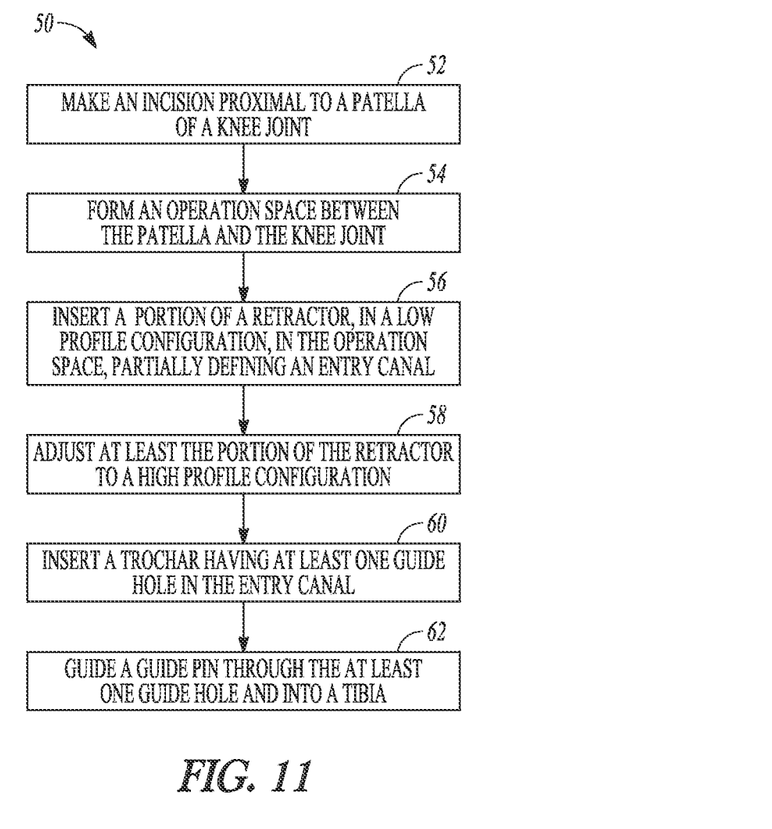
FIG. 11 is a flow chart illustrating a method of guiding a guide pin into a tibia, in accordance with a t least one example of the present invention.

FIG. 11 is a flow chart illustrating an example method 50 of guiding a guide pin into a tibia of a knee joint positioned in flexion. At 52, an incision proximal to a patella can be made. The incision can be made about 2 finger widths, or at about 1.5 centimeters, above a superolateral corner of the patella. At 54, an operation space can be formed between the patella and the knee joint. Forming the operation space can include pulling or pushing the patella away from or anterior to the knee joint, such as by a surgeon inserting one or more fingers through the incision and into a cavity of the knee joint, to loosen at least a portion of viscoelastic tissue connected to the patella. At 56, a retractor, in a low profile configuration, can be inserted into the operation space. The retractor can define an entry canal configured to receive other components of a suprapatellar system, such as a reamer. At 58, the retractor can be expanded from the low profile configuration, defining a first cross-sectional diameter, to a high profile configuration, defining a larger second cross-sectional diameter.

The method 50 can further include inserting a trocar in at least a portion of the entry canal, at 60. In an example, a tube can be inserted in at least a portion of the entry canal and the trocar can be inserted in the tube. In an example, an outside diameter of the tube can be minimized to reduce the size of the operation space. The trocar can include at least one guide hole configured to receive a guide pin. At 62, the guide pin can be inserted into the tibia by way of the trocar. In an example, the method 50 can include adjusting a position of the guide pin to an adjusted position. The adjusted positioned can be about 2 millimeters or more in at least one of a medial-lateral direction and an anterior-posterior direction to define an approximate center of a tibial canal. Adjusting the position of the guide pin can be aided by x-ray or fluorescence imaging.

Figure 12:
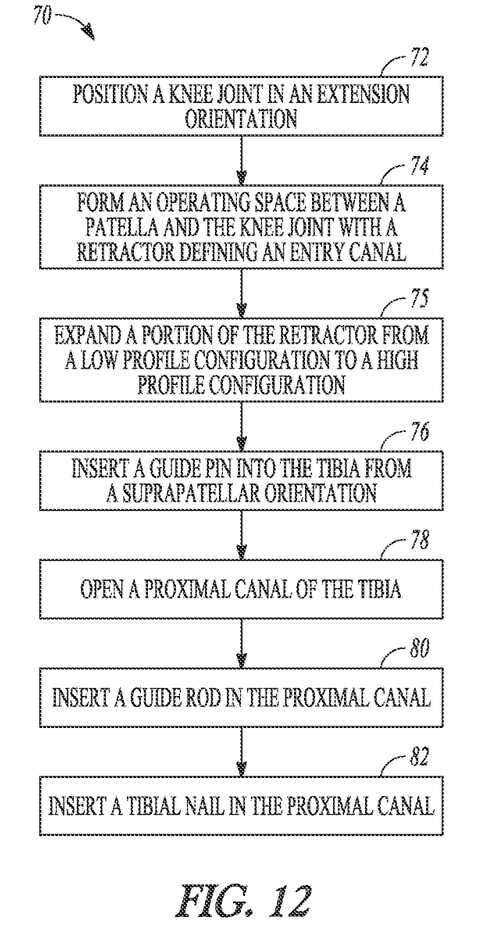
FIG. 12 is a flow chart illustrating a suprapatellar method of inserting a tibial nail, in accordance with a t least one example of the present invention.

FIG. 12 is a flow chart illustrating an example suprapatellar method 70 of inserting a tibial nail. At 72, a knee joint can be positioned in the extension orientation, such as within about 10 to 15 degrees of flexion, to at least relax a quadriceps muscle and substantially prevent a procurvatum deformity. At 74, an operation space can be formed between a patella and a knee joint from the suprapatellar direction, such as behind the posterior side of the patella. At 75, a portion of the retractor can be expanded from a low profile configuration, in which the entry canal has a first diameter, to a high profile configuration, in which the entry canal has a larger second diameter. At 76, a guide pin can be inserted at least partially into a tibia through at least a portion of the operation space.

The method 70 can further include opening a proximal canal, at 78, using at least one of an entry reamer or an entry awl inserted in a portion of the tibia from the suprapatellar direction. At 80, a guide rod can be inserted in at least a portion of the proximal canal. In an example, a tibial nail length measurement can be taken by a nail length gauge inserted through a tube, as described above. A reduction rod can also be inserted through the tube to reduce a fracture of the tibia. The method 70 can include reaming the proximal canal with a reamer guided over the guide rod. In an example, the reamer can be part of a Pressure Sentinel® intramedullary reaming system produced by Zimmer, Inc., of Warsaw, Ind. Pressure Sentinel® is a registered trademark of Zimmer Technology, Inc. At 82, the tibial nail can be inserted in at least the portion of the proximal canal. Further, the tibial nail can be fixed by one or more tibial retention nails or screws.

Figure 13:
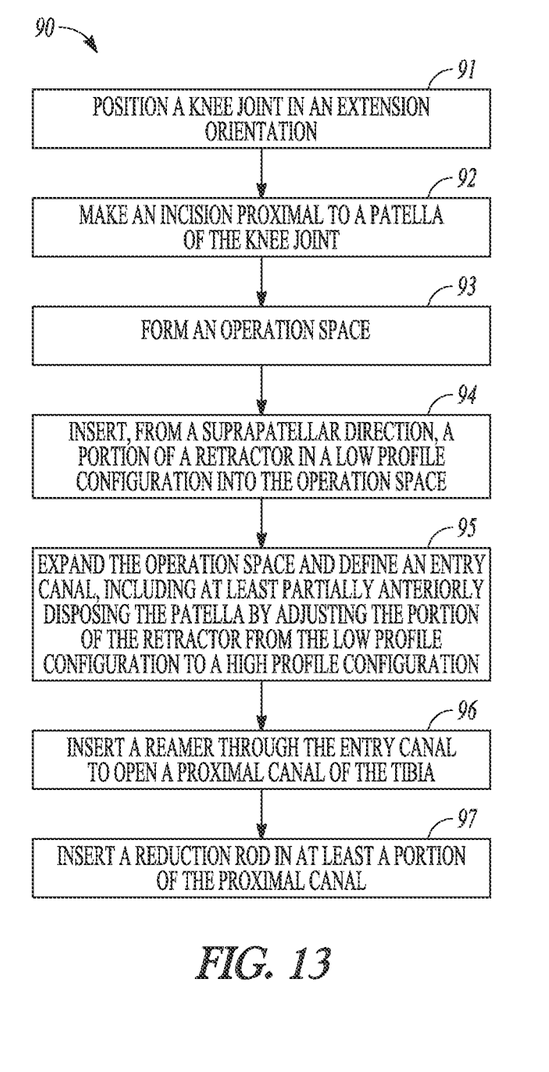
FIG. 13 is a flow chart illustrating a method of reducing a tibial fracture from a suprapatellar direction, in accordance with a t least one example of the present invention.

FIG. 13 is a flow chart illustrating an example method 90 of reducing a tibial fracture from a suprapatellar direction. At 91, a knee joint can be positioned in an extension orientation. At 92, an incision, such as a skin incision that cuts through a portion of a quadriceps tendon, can be made. The method 90 can include forming an operation space from the incision to between at least a portion of a patella and a compartment of the knee joint, at 93. At 94, a refractor, in a low profile configuration, can be inserted in at least a portion of the operation space to define an entry canal of a first diameter.

The method 90 can further include expanding the operation space by at least partially anteriorly displacing the patella from the compartment of the knee joint, at 95. Expanding the operation space can include anteriorly expanding the retractor from the low profile configuration to a high profile configuration defining a second diameter greater than the first diameter. Further, at 96, a tibia can be reamed by inserting a reamer through an entry canal to open a proximal canal of the tibia. The reamer can include an outer diameter of up to about 15 millimeters. At 97, a reduction rod can be inserted in at least a portion of the proximal canal. The reduction rod can be used to reduce the tibial fracture.

The above Detailed Description includes references to the accompanying drawings, which form a part of the Detailed Description. The drawings show, by way of illustration, specific examples in which the invention can be practiced. These examples are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above Detailed Description is intended to be illustrative, and not restrictive. For example, the above-described examples (or one or more aspects thereof) may be used in combination with each other. Other examples can be used, such as by one of ordinary skill in the art upon reviewing the above Detailed Description. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the Detailed Description as examples or examples, with each claim standing on its own as a separate example, and it is contemplated that such examples can be combined with each other in various combinations or permutations. The scope of the invention should be determined with reference to the appended claims, along with the full scope of equivalents to which such claims are entitled.

The Abstract is provided to comply with 37 C.F.R. §1.72 (b), to allow the reader to quickly ascertain the nature of the technical disclosure. It is submitted with the understanding that it will not be used to interpret or limit the scope or meaning of the claims.

What is claimed is:

1. A method, comprising:
   making an incision proximal to a patella of a knee joint;
   forming an operation space between the patella and the knee joint;
   inserting a portion of a retractor, in a low profile configuration, in the operation space, including partially defining an entry canal through the operation space, wherein the retractor includes an upper convex section with an outer concave surface configured to receive the posterior side of a patella and a lower opposing convex section, wherein inserting the portion of the retractor in the operation space includes engaging the outer concave surface of the retractor with a posterior side of the patella;
   adjusting at least the portion of the retractor in the operation space from the low profile configuration to a high profile configuration, wherein the adjusting includes separating the upper convex section from the lower opposing convex section;
   inserting a trocar having at least one guide hole in the entry canal; and
   guiding a guide pin through the at least one guide hole and into a tibia.

2. The method of claim 1, wherein adjusting the retractor from the low profile configuration to the high profile configuration includes expanding the operation space in at least one of an anterior-posterior direction or a medial-lateral direction.

3. The method of claim 1, wherein adjusting the retractor from the low profile configuration to the high profile configuration includes increasing a diameter of the entry canal.

4. The method of claim 1, wherein adjusting the retractor from the low profile configuration to the high profile configuration includes increasing a spacing been a posterior side of the patella and an adjacent surface of the tibia or a femur.

5. The method of claim 1, wherein adjusting the retractor from the low profile configuration to the high profile configuration includes stretching one or more viscoelastic tissues associated with the patella.

6. The method of claim 1, further comprising adjusting the retractor from the high profile configuration to the low profile configuration and removing the retractor from the operating space.

7. The method of claim 1, further comprising placing the knee joint in an extension position prior to making the incision, including forming an angle of about 150 degrees or more between a femur and the tibia.

8. The method of claim 1, wherein making the incision proximal to the patella includes making an incision at least 1.5 centimeters proximal to the patella.

9. The method of claim 1, wherein making the incision proximal to the patella includes making an incision in a quadriceps tendon.

10. The method of claim 1, further comprising inserting a tube in the entry canal prior to inserting the trocar, and wherein inserting the trocar includes inserting the trocar in the tube.

11. The method of claim 1, further comprising adjusting a position of the guide pin, including moving the guide pin at least about 2 millimeters in at least one of a medial-lateral direction or an anterior-posterior direction.

12. The method of claim 1, wherein forming the operation space includes loosening at least a portion of one or more viscoelastic tissues connected to the patella.

13. A method, comprising:
    positioning a knee joint in an extension orientation;
    forming an operation space between a patella and the knee joint from a suprapatellar direction with a retractor defining an entry canal, wherein the retractor includes an upper convex section with an outer concave surface configured to receive the posterior side of a patella and a lower opposing convex section, and wherein forming the operation space includes engaging the concave outer surface of the retractor with a posterior side of the patella;

expanding a portion of the retractor from a low profile configuration, in which the entry canal has a first diameter, to a high profile configuration, in which the entry canal has a larger second diameter, wherein the expanding includes separating the upper convex section from the lower opposing convex section;

inserting a guide pin through the entry canal and into at least a portion of a tibia through at least a portion of the operation space from the suprapatellar direction;

opening a proximal canal of the tibia;

inserting a guide rod in at least a portion of the proximal canal; and inserting a tibial nail in the portion of the proximal canal.

14. The method of claim 13, wherein opening the proximal canal includes using at least one of an entry reamer or an entry awl inserted in a portion of the tibia from the suprapatellar direction.

15. The method of claim 13, further comprising measuring a tibial nail length with a nail length gauge.

16. The method of claim 13, further comprising reducing a fracture of the tibia.

17. The method of claim 13, further comprising reaming the opened proximal canal with a reamer guided over the guide rod.

18. A method, comprising:

positioning a knee joint in an extension orientation;

making an incision proximal to a patella of the knee joint;

forming an operation space, using the incision, between a portion of the patella and a compartment of the knee joint;

inserting, from a suprapatellar direction, a portion of a retractor in a low profile configuration into the operation space wherein the retractor includes an upper convex section with an outer concave surface configured to receive the posterior side of a patella and a lower opposing convex section, and wherein inserting the portion of the retractor includes engaging the concave outer surface of the retractor with a posterior side of the patella;

expanding the operation space and defining an entry canal, including at least partially anteriorly disposing the patella from the compartment of the knee joint by adjusting the portion of the retractor from the low profile configuration to a high profile configuration, wherein the adjusting includes separating the upper convex section from the lower opposing convex section;

inserting a reamer through the entry canal to open a proximal canal of the tibia; and inserting a reduction rod in at least a portion of the proximal canal.

19. The method of claim 18, wherein expanding the operation space includes resting a portion the retractor on a femur and anteriorly adjusting an opposing portion of the retractor.

20. The method of claim 1, further comprising measuring, with a tension gauge coupled to the retractor, a compression force exerted on the refractor.

\* \* \* \* \*